United States Patent [19]

Hyde et al.

[11] Patent Number: 4,642,403
[45] Date of Patent: Feb. 10, 1987

[54] PRODUCTION OF AROMATICS FROM ETHANE AND/OR ETHYLENE

[75] Inventors: Edward A. Hyde, Send Marsh; Timothy K. McNiff, Weybridge, both of England

[73] Assignee: The British Petroleum Company p.l.c., London, England

[21] Appl. No.: 861,071

[22] Filed: May 8, 1986

Related U.S. Application Data

[63] Continuation-in-part of Ser. No. 788,338, Oct. 17, 1985.

[30] Foreign Application Priority Data

Nov. 16, 1984 [GB] United Kingdom ............... 8429007

[51] Int. Cl.$^4$ .............................................. C07C 12/02
[52] U.S. Cl. .................................... 585/415; 585/417
[58] Field of Search ................................ 585/415, 417

[56] References Cited

U.S. PATENT DOCUMENTS

| | | |
|---|---|---|
| 3,855,115 | 12/1974 | Morrison . |
| 4,056,575 | 1/1977 | Gregory et al. ................ 585/417 |
| 4,120,910 | 10/1978 | Chu . |
| 4,350,835 | 9/1982 | Chester et al. ................ 58/417 |
| 4,490,569 | 12/1984 | Chu et al. ................ 585/415 |
| 4,497,970 | 2/1985 | Young ................ 585/417 |

Primary Examiner—Curtis R. Davis
Attorney, Agent, or Firm—Brooks Haidt Haffner & Delahunty

[57] ABSTRACT

This invention relates to a process for producing aromatic hydrocarbons by bringing a feedback containing at least 10% w/w of $C_2$ hydrocarbons into contact with a catalyst composition comprising a gallium loaded ziolite and a Group VIII metal selected from rhodium and platinum. The reaction is carried out at a temperature from 500°–750° C. A WHSV of 0.2–10 and a pressure of 1–20 bar are preferred. The presence of Group VIII metal increases conversion of the $C_2$ feed reduces formation of undesirable polynuclear aromatics.

10 Claims, No Drawings

PRODUCTION OF AROMATICS FROM ETHANE AND/OR ETHYLENE

The present invention relates to a process for producing aromatic hydrocarbons from a hydrocarbon feedstock rich in $C_2$ hydrocarbons and is a continuation-in-part of copending U.S. application Ser. No. 788,338, filed on Oct. 17, 1985.

Hitherto synthetic routes to producing aromatics from open chain hydrocarbons have started from feedstocks which have at least three carbon atoms. Such feedstocks are initially dimerised and the dimerised product is subsequently cyclised over a variety of catalysts at temperatures in the region of 500°–600° C. Such processes are described for example in our British Pat. Nos. 1507778 and 1561590. According to the British Pat. No. 1561590 a gallium catalyst supported on an aluminosilicate in which the ratio of silica to alumina is between 20:1 and 70:1 is used.

Our published EP No. 0050021 discloses a process for producing aromatics from $C_2$ hydrocarbons, especially ethane, by bringing the hydrocarbon feed into contact with a gallium/zeolite catalyst at elevated temperature.

It has now been found that by incorporating into the gallium/zeolite catalyst small amounts of a Group VIIB or a Group VIII metal the activity of the catalyst for the conversion of $C_2$ hydrocarbons is substantially increased in terms of (a) increased conversion at a given temperature, or (b) achieving a given conversion at a lower temperature than used hitherto, and (c) reduction in the formation of undesirable polynuclear aromatics in the process.

Accordingly, the present invention is a process for producing aromatic hydrocarbons comprising bringing into contact in the vapour phase at a temperature from 500° C. to 750° C. a hydrocarbon feedstock containing at least 10% by weight of $C_2$ hydrocarbons with a catalyst composition comprising (i) an aluminosilicate loaded with gallium as a gallium compound and/or as gallium ions and having a silica to alumina molar ratio of at least 5:1, and (ii) a Group VIII a metal selected from rhodium and platinum.

The Periodic Table referred to herein and throughout the specification is the Table at pages 448 and 449 of the Handbook of Chemistry and Physics, 44th Edition, Ed. Hodgman, C. D. et al and published by The Chemical Rubber Publishing Co., Ohio, USA.

The $C_2$ hydrocarbon in the feedstock may be ethane, ethylene or mixtures thereof. The feedstock may contain in addition other open chain hydrocarbons containing between 3 and 8 carbon atoms as coreactants or a diluent which is inert under the reaction conditions. Specific examples of such additional coreactants are propane, propylene, n-butane, isobutane, n-butenes and isobutene. The hydrocarbon feedstock contains at least 10%, suitably at least 50%, preferably at least 70% by weight of $C_2$ hydrocarbons.

The aluminosilicate may be loaded with gallium by methods well known to those skilled in the art. Such methods are described for instance for our published EP-A-24930. Gallium is preferably present as gallium oxide in the catalyst composition.

The aluminosilicates loaded with gallium are preferably zeolites of an MFI or MEL type structures (cf. "Chemical Nomenclature, and Formulation of Compositions, of Synthetic and Natural Zeolites," IUPAC yellow booklet, 1978, and zeolite structure types published by The Structure Commission of the International aeolite Association entitled "Atlas of Zeolite Structure Types", by Meier, W. M. and Olsen, D. H. (1978), distributed by Polycrystal Book Service, Pittsburgh, Pa, USA). The zeolites suitably have a silica to alumina ratio of between 20:1 and 150:1 and may be selected from zeolites of the general formula: $M_{2/n}O.Al_2O_3.ySiO_2.zH_2O$ wherein M is a cation which is a positively charged ion selected from a metal ion or an organic ion of valence n and a proton, y is an integer greater than 5 and z is from 0 to 40. The metal cation, M, is preferably an alkali metal or alkaline earth metal ion, preferably sodium or potassium ions. The organic cations may be represented by the formula $R^1R^2R^3R^4N^+$ or by an ion derived from the amine $R^1R^2R^3N$, the diamine $R^1R^2N(CH_2)_xNR^3R^4$ or pyrrolidine where $R^1R^2R^3$ and $R^4$ may be H, $CH_3$, $C_2H_5$, $C_3H_7$, $C_4H_9$ or $-CH_2CH_2OH$ and x equals 2, 3, 4, 5 or 6. A typical example of the MFI zeolite is ZSM-5 though other zeolites of the ZSM variety, for example ZSM-8, ZSM-11, ZSM-12 and ZSM-35 may also be used. These are extensively described in a number of publications including U.S. Pat. No. 3,970,544 (Mobil). These zeolites are ususally produced from a silica source, an alumina source, an alkali metal hydroxide and a nitrogen containing base as template. The nitrogen-containing base may be organic such as an alkanolamine, for example diethanolamine, or inorganic, e.g. ammonia. Zeolites made in this manner are described in our published EP-A-Nos. 0002899, 0002900 and 0030811. Zeolites derived by process of EP-A-30811 are preferred.

The Group VIII metal selected from rhodium and platinum may be incorporated into the catalyst composition by impregnation or ion-exchange using a compound of the metal. Specifically, the Group VIII metals rhodium and platinum are present in the active catalyst composition in their metallic state irrespective of the type of compound or salt of the metal used for loading the zeolite. These metals may be suitably provided from a solution e.g. aqueous solution, of the respective metal salt such as for instance rhodium trihalide e.g. trichloride, or chloroplatinic acid. Alternatively the gallium loaded zeolite may be intimately mixed with an appropriate compound of rhodium or platinum.

The aluminosilicate may be loaded with the compounds of gallium and the Group VIII metal in either order or a mixture of the two compounds may be used for simultaneous loading of the aluminosilicate. It is preferable to load the aluminosilicate with the Group VIII metal compound prior to loading with gallium.

Whichever method of catalyst preparation is used, the amount of gallium present in the catalyst compositions may vary for instance from 0.05 to 10% by weight of the total aluminosilicate in the catalyst composition. The gallium exchanged or impregnated zeolite thus obtained may be combined with a porous matrix material, e.g. silica or alumina or other inorganic compositions prior to contact with the feedstock to improve the mechanical strength of the catalyst.

The amount of Group VIII metal present in the catalyst composition is suitably from 0.05 to 10%, preferably from 0.1 to 0.8% w/w of the total composition.

The catalyst composition may be activated prior to contact with the hydrocarbon feedstock. The activation may be carried out by heating the catalyst at a temperature from 400° C. to 650° C., preferably from 500° C. to 600° C. Activation may be carried out in an atmosphere of hydrogen, air, steam or a gas inert under the reaction conditions such as nitrogen but preferably in an atmosphere containing oxygen. The activation may be carried out in the reactor itself prior to the reaction. The catalyst composition is suitably used in a fixed bed, a moving bed or a fluidised bed.

The hydrocarbon feedstock is thereafter contacted in the vapour phase with the catalyst composition at a temperature from 500° to 750° C. preferably from 525° to 600° C. in an inert atmosphere in the absence of oxygen. The inert atmosphere may be provided by a gas inert under the reaction conditions such as nitrogen distillation.

The reaction is suitably carried out at a WHSV for the reaction of 0.2 to 10, preferably from 0.5 to 2.0.

The reaction pressure is suitably from 1-20 bar, preferably from 1-10 bar.

Any unreacted $C_2$ hydrocarbon feedstock e.g. ethane or ethylene is recovered from the reaction products and may be recycled to the reaction along with the fresh hydrocarbon feedstock to be aromatised.

The invention is further illustrated with reference to the following Examples and Comparative Tests.

In the Examples and Comparative Tests and liquid products of the reaction were identified by on-line dual column GC using a POROPAK QS column for the gaseous products from hydrogen to aromatics and a OV101 silicone gum rubber (SGR) column for the aromatics.

EXAMPLES

A. "Standard" Ga/Zeolite Preparation

ZSM-5 zeolite, in the as-synthesized Na+ form, having a silica/alumina ratio in the framework of 35.8 (as determined by MASNMR), was acid washed in 5% nitric acid at room temperature for ½ hour, filtered and washed again with distilled water. This material was then ammonium exchanged twice by refluxing in 1M $NH_4NO_3$(aq), filtering and water washing. The zeolite was then impregnated with gallium from a gallium nitrate solution whose pH had been adjusted to between 2 and 3 by addition of ammonia. The Ga/NH$_4$-MFI zeolite was then bound with Ludox 'AS 40' silica gel to give 28.6 wt% silica as binder. The bound material was sieved to between 12 and 30 mesh sizes. The catalyst particles were then charged to a tubular reactor and treated for 2 hours in 16 vol/vol % steam in air at -550° C.

B. Catalyst Compositions Used:

Example 1

The standard Ga/zeolite referred to in Section A above was impregnated with an aqueous solution of chloroplatinic acid.

Examples 2 and 3

The standard Ga/zeolite referred to in Section A above was impregnated with an aqueous solution of [Rh(NH$_3$)$_5$Cl]Cl$_2$.

Comparative Test (not according to the invention)

The standard Ga/zeolite referred to in Section A above was impregnated with an aqueous solution of ammonium chloride.

C. Hydrocarbon Conversion Process

The catalysts in Examples 1-3 and in the Comparative Test shown in Section B above were each subjected to in-situ hydrogen treatment for 2 hours at 550° C. prior to testing for hydrocarbon conversion activity. The hydrocarbon feedstock used in Example 2 and the Comparative Test contained more than 99.35 vol % of ethane, whereas the feedstock used in Examples 1 and 3 contained 95 vol % ethane, 3 vol % propane and 2 vol % propane. The aromatisation activity was tested using a 20 ml catalyst charges in annular stainless steel reactors. The reaction conditions used and the results achieved are tabulated below:

| Example | Comparative Test | | 1 | |
|---|---|---|---|---|
| Metals (wt %'s) | Ga (0.8) | | Ga (0.8) Pt (1.25) | |
| Reaction Temp (°C.) | 550 | | 550 | |
| Pressure (bar abs) | 6 | | 6 | |
| WHSV (wrt ethane) | 1 | | 0.9 | |
| t/hrs on stream | 3 | 22.5 | 3.5 | 23 |
| $C_2H_6$ conversion (wt %) | 23.7 | 18.1 | 37.3 | 31.8 |
| Selectivity to aromatics (wt %*) | 49.3 | 48.4 | 48.0 | 52.5 |
| Yield of aromatics (wt %) | 11.7 | 8.8 | 17.9 | 16.7 |
| Productivity (g l$^{-1}$hr$^{-1}$) | 76 | 57 | 110 | 103 |

| Example | 2 | | 3 | |
|---|---|---|---|---|
| Metals (wt %) | Ga (0.8) Rh (0.7) | | Ga (0.8) Rh (0.7) | |
| Reaction Temp (°C.) | 550 | | 550 | |
| Pressure (bar abs) | 6 | | 6 | |
| WHSV (wrt ethane) | 1 | | 0.9 | |
| t/hrs on stream | 3 | 22.5 | 3 | 22.5 |
| $C_2H_6$ conversion (wt %) | 37.4 | 33.1 | 35.2 | 30.6 |
| Selectivity to aromatics (wt %*) | 42.9 | 45.0 | 52.0 | 55.9 |
| Yield of aromatics (wt %) | 16.0 | 14.9 | 18.3 | 17.1 |
| Productivity (g l$^{-1}$hr$^{-1}$) | 103 | 96 | 112 | 105 |

*Yield of aromatics × 100/$C_2H_6$ conversion

We claim:

1. A process for producing aromatic hydrocarbons, said process comprising bringing into contact in the vapour phase at a temperature from 500°-750° C. a hydrocarbon feedstock containing at least 10% by weight of $C_2$ hydrocarbons with a catalyst composition comprising (i) an aluminosilicate loaded with gallium as a gallium compound and/or as gallium ions and having a silica to alumina molar ratio of at least 5:1, and (ii) a Group VIII metal selected from rhodium and platinum.

2. A process according to claim 1 wherein the hydrocarbon feedstock contains at least 50% by weight of $C_2$ hydrocarbons.

3. A process according to claim 1 or 2 wherein the aluminosilicate loaded with gallium is an MFI or an MEL type zeolite.

4. A process according to claim 1 or 2 wherein gallium is present in an amount from 0.05 to 10% by weight of the total catalyst composition.

5. A process according to claim 1 or 2 wherein the Group VIII metal is present in an amount from 0.05 to 10% by weight of the total catalyst composition.

6. A process according to claim 1 or 2 wherein the catalyst composition is activated by heating at a temperature from 400° to 650° C. prior to contact with the hydrocarbon feedstock.

7. A process according to claim 1 or 2 wherein the hydrocarbon feedstock is brought into contact with the catalyst composition at a WHSV from 0.2-10 and a pressure from 1-20 bar.

8. A process according to claim 1 or 2 wherein the hydrocarbon feedstock is brought into contact with the catalyst composition at a temperature from 525°-600° C.

9. A process according to claim 1 or 2 wherein the catalyst composition is combined with a porous matrix material prior to contact with the feedstock.

10. A process according to claim 1 or 2 wherein unreacted $C_2$ hydrocarbons are recovered from the reaction products and are recycled along with the fresh hydrocarbon feedstock to be aromatised.

* * * * *